United States Patent [19]
Sakurai et al.

[11] Patent Number: 5,550,292
[45] Date of Patent: Aug. 27, 1996

[54] BENZYLAMINE DERIVATIVES

[75] Inventors: Yohji Sakurai; Nobuyuki Kurahashi, both of Tokushima; Tsuyoshi Hirose, Kagawa; Takashi Miwa, Tokushima; Atsushi Mori, Tokushima; Takao Nishi, Tokushima, all of Japan

[73] Assignee: Otsuka Pharmaceutical Co., Ltd., Tokyo, Japan

[21] Appl. No.: 428,114

[22] PCT Filed: Aug. 11, 1994

[86] PCT No.: PCT/JP94/01332

§ 371 Date: Apr. 28, 1995

§ 102(e) Date: Apr. 28, 1995

[87] PCT Pub. No.: WO95/06630

PCT Pub. Date: Mar. 9, 1995

[30] Foreign Application Priority Data

Aug. 30, 1993 [JP] Japan ................................. 5-214147
Mar. 15, 1994 [JP] Japan ................................. 6-044003

[51] Int. Cl.$^6$ ............................................. C07C 217/58
[52] U.S. Cl. ..................... 564/399; 564/385; 564/386; 564/390
[58] Field of Search ........................ 564/385, 386, 564/389, 390

[56] References Cited

U.S. PATENT DOCUMENTS 4,687,865  8/1987  Thottathil ........................... 549/463

FOREIGN PATENT DOCUMENTS

| 0303961A2 | 2/1989 | European Pat. Off. . |
| 6-25129 | 2/1994 | Japan . |
| WO90/14334 | 11/1990 | WIPO . |
| WO91/09594 | 7/1991 | WIPO . |
| WO93/00313 | 1/1993 | WIPO . |
| WO93/07113 | 4/1993 | WIPO . |

OTHER PUBLICATIONS

"The Place of the SSRIs and Fluvoxamine in the Treatment of Patients with Depression", Y. Lecrubier, Drugs 43 (2): 1–2 (1992).
"Pharmacological Differences of Serotonin Reuptake Inhibitors and Possible Clinical Relevance", B. E. Leonard, Drugs 43 (2): 3–10 (1992).
"Comparative Efficacy of Antidepressants", S. Kasper et al., Drugs 43 (2) pp. 11–23 (1992).
"The Synthesis of a Conformationally Rigid Calcium Channel Blocker", J. C. Barrish et al., Chemical Abstracts 119:203257n (1993).

*Primary Examiner*—Richard L. Raymond
*Attorney, Agent, or Firm*—Finnegan, Henderson, Farabow, Garrett & Dunner

[57] ABSTRACT

A benzylamine derivative or salt thereof having antidepressant and antianxiety activities having the general formula:

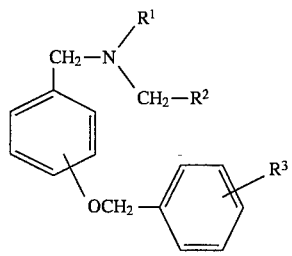

wherein
  $R^1$ is a lower alkyl group;
  $R^2$ is a cycloalkyl group; and
  $R^3$ is a halogen atom;
or salt thereof.

13 Claims, No Drawings

BENZYLAMINE DERIVATIVES

This application is a 371 of PCT/JP94/01332, filed Aug. 11, 1994.

FIELD OF THE INDUSTRIAL UTILIZATION

The present invention relates to novel benzylamine derivatives and their salts.

BACKGROUND ART

As to the current human society is becoming increasingly complex in structure and mechanism, so that people undergo increasing stresses of various kinds. In such an ever-changing society, the number of people suffering from mental disorder, particularly depression and anxiety neurosis are increasing, posing a big social problem.

Unlike the typical depression seen in the past, depression appearing currently is relatively slight and tends to become chronic, in many cases. Depression is often difficult to distinguish from neurosis and tends to become chronic. It is reported that most of the patients of chronic depression have neurosis as well and that the number of depression patients is increasing more and more in recent years (cf. Japanese Journal of Clinical Psychiatry, Vol. 21, No. 4, pp. 691–695, 1992).

Thus, the features of mental disorder are becoming more complex as the structure and mechanism of society become complex. The following two facts are pointed out as the recent major changes in the features of metal disorder.

(1) In neurosis, those neuroses are increasing which show depressive syndrome and which are difficult to distinguish from depression.

(2) Among the patients which have been judged to have neurosis, patients of slight depression are included. Among, in particular, the patients which have been judged to have neurosis because of their anxiety attack and expectation fear, patients of slight depression are included at a fairly high ratio (cf. Japanese Journal of Clinical Psychiatry, Vol. 21, No. 4, pp. 691–695, 1992).

According to a clinical research (cf. "Anxious Depression" edited by Racagni G. Smeraldi, Raven Press, N.Y., 1987), analysis of the symptoms of the patients who had been judged to have serious depression, indicated that the symptoms comprised worry of intermediate level (72%), psychological anxiety (62%), physical anxiety (of autonomic nervous system and muscle system) (42%), fear attack (29%), fear symptom (19%) and obsessive-compulsive symptom (1.2%). Patients of depression include patients of anxiety symptom at a high ratio.

Mental disorder which show complex and diversified symptoms as mentioned above, are currently treated, in many cases, with an antidepressant, an antianxiety agent or a combination thereof, depending upon the symptoms. Such treatment is effective in some cases but is said to be insufficient in most cases. Conventional antidepressants are effective for endogeneous depression, but are not sufficiently effective for character-originated depression or highly neurotic depression (cf. Journal of Neuropsychopharmacology, Vol. 9, No. 4, pp. 279–285, 1987). Use of antianxiety agent by patients who show anxiety symptom on the surface while actually having a depressive phase, prolongs the depression in some cases (cf. Japanese Journal of Clinical Psychiatry, Vol. 21, No. 4, pp. 691–695, 1992). Use of antidepressant based on the indiscreet judgement by clinical department other than psychiatry department, may overlook suicidal ideation and induce the prolongation of depression (cf. Journal of Neuropsychopharmacology, Vol. 9, No. 4, pp. 279–285, 1987).

Conventional antidepressants have problems; that is, (1) they show no immediate effect and need to be administered continuously for at least 2 weeks, (2) they have undesirable side effects such as anti-cholinergic effect and the like and (3) they are ineffective in some cases (effective ratio: 65%) (cf. Journal of Neuropsychopharmacology, Vol. 11, No. 10, pp. 753–761, 1989). Conventional antianxiety agents have problems; that is, (1) they have side effects such as excessive sedation, somnolence, muscle relaxation and the like and (2) there often appear serious adverse symptoms such as dependency, abstinence symptom, memory impairment and the like (cf. Journal of Neuropsychopharmacology, Vol. 11. No. 9, pp. 709–719, 1989).

Single or combination use by patients, of antidepressant and antianxiety agent which, as mentioned above, have many side effects and many adverse effects and are said to be ineffective to the core symptoms of mental disorder, is considered to produce antinomy in the treatment of mental disorder. Hence, if there is developed a medicine which tackles the root cause of mental disorder and which shows both an anti-depression activity and an anti-anxiety activity, it will solve the above-mentioned problems associated with the treatment of mental disorder.

Compounds having chemical structures similar to those of the benzylamine derivatives of the present invention are disclosed in PCT International Applications WO 90/14334 (Publication Date: Nov. 29, 1990), WO 93/07113 (Publication date: Apr. 15, 1993), WO 91/09594 (Publication Date: Jul. 11, 1991) and WO 93/00313 (Publication Date: Jan. 7, 1993). Particularly in WO 91/09594 and WO 93/00313 are disclosed compounds represented by the following general formula:

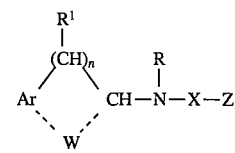

wherein:

Ar is aryl or heteroaryl wherein aryl or heteroaryl can be substituted by hydrogen, halogen such as chloro, fluoro, bromo or iodo, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamino, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3$–$C_6$ heterocycloalkyl, a $C_3$–$C_6$ heterocycloalkyl ring fused to a benzene ring, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro or $C_2$–$C_{15}$ dialkylsulfamoyl;

R is hydrogen or $C_1$–$C_6$ alkyl;

$R^1$ is selectively from the group consisting of hydrogen, $C_1$–$C_6$ alkyl, hydroxy, amino, $C_1$–$C_6$ alkylamino and =O (a double bond oxygen); or R and R¹ together form a morpholino ring;

n is 0–5;

W is —(CH$_2$)$_p$— or —H H— wherein p is 1–3;

X is —(CH$_2$)$_q$— wherein q is 1–6, —(CH$_2$)$_r$—C≡C—(CH$_2$)$_r$— wherein each r is 0–3, —(CH$_2$)$_r$—CH=CH—(CH$_2$)$_r$—,

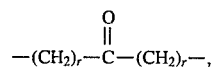

—(CH$_2$)$_r$—Y—(CH$_2$)$_r$— wherein Y is O or S, or C$_1$–C$_6$ alkyl (wherein Z is hydrogen); and Z is hydrogen, aryl, an aryl-substituted carboxylic acid group, heteroaryl or cycloalkyl, wherein aryl, heteroaryl and cycloalkyl can be substituted by hydrogen, halogen such as chloro, fluoro, bromo or iodo, CF$_3$, C$_1$–C$_6$ alkoxy, C$_2$–C$_6$ dialkoxymethyl, C$_1$–C$_6$ alkyl, cyano, C$_3$–C$_{15}$ dialkylaminoalkyl, carboxy, carboxamido, C$_1$–C$_6$ haloalkyl, C$_1$–C$_6$ haloalkylthio, allyl, aralkyl, C$_3$–C$_6$ cycloalkyl, aroyl, aralkoxy, C$_2$–C$_6$ carboxylic acyl, acyl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, C$_3$–C$_6$ heterocycloalkyl, a C$_3$–C$_6$ heterocycloalkyl ring fused to a benzene ring, C$_1$–C$_6$ alkylthio, C$_1$–C$_6$ alkylsulfonyl, C$_1$–C$_6$ haloalkylsulfonyl, C$_1$–C$_6$ alkylsulfinyl, C$_1$–C$_6$ haloalkylsulfinyl, arylthio, C$_1$–C$_6$ haloalkoxy, amino, C$_1$–C$_6$ alkylamino, C$_2$–C$_{15}$ dialkylamino, hydroxy, carbamoyl, C$_1$–C$_6$ N-alkylcarbamoyl, C$_2$–C$_{15}$ N,N-dialkylcarbamoyl, nitro, C$_2$–C$_{15}$ dialkylsulfamoyl or an ortho methylenedioxy group.

According to said two literatures, the compounds of the above general formula are useful as a sigma-receptor ligand and can be used as a drug for schizophrenia or other psychosis, or for the treatment of central nervous system diseases, drug abuse, gastrointestinal diseases, hypertension, migrane, peritonsilitis, depression, etc.

Thus, the above-mentioned literatures disclose compounds having chemical structures similar to those of the present benzylamine derivatives, but do not disclose the present benzylamine derivatives per se.

Under the above situation, the present inventors made an extensive study and found out that the benzylamine derivatives represented by the above general formula (1) and their salts have both an anti-depression activity and an anti-anxiety activity and are effective as an excellent anti-depression and anti-anxiety drug. The present invention has been completed based on the finding. The benzylamine derivatives and their salts according to the present invention are characterized in that they are effective for amelioration of consciousness disturbance as well as for the treatment of obsessive-compulsive neurosis.

DISCLOSURE OF THE INVENTION

The benzylamine derivatives of the present invention are novel compounds not yet reported in any literature and are represented by the following general formula (1):

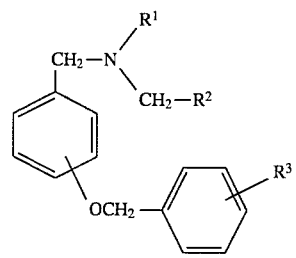

wherein R$^1$ is a lower alkyl group; R$^2$ is a cycloalkyl group; and R$^3$ is a halogen atom.

The benzylamine derivatives represented by general formula (1) and their salts according to the present invention have both an anti-depression activity and an antianxiety activity and are effective as an excellent antidepression and anti-anxiety agent responding to the demand in medical care.

The benzylamine derivatives or their salts according to the present invention, having, in particular, an effect for activating the central nervous system and an effect for ameliorating disturbance of consciousness, are useful as a remedy for head trauma, cerebral hemorrhage, cerebral infarction, subarachnoidal hemorrhage, medical poisoning, atmospheric hypoxia, accident caused by anoxia, disturbance of consciousness after operation of the brain or after bypass operation of the heart, and the sequelae of said diseases such as mental growth retardation, lowering of attention response, language disorder, recognition disturbance, learning disability, hypokinetic syndrome, hypobulia, emotional disturbance and the like, and are also useful as an agent for ameliorating various diseases such as depressive state in senile dementia, delirium, language disorder, recognition disturbance, learning disability, hypokinetic syndrome, lowering of attention response, memory impairment with aging and the like. Further, the compounds of the present invention have a sigma receptor-agonistic action and are useful as a remedy for depression, anxiety neurosis, psychotic diseases caused by stress (e.g. psychosomatic disease), anorexia nervosa, hypopituitarism, hyperprolactinemia, cerebrovascular dementia, hyperkinetic syndrome, dementia-amnesia, Perkinson disease and the like. The compounds of the present invention can also be used as an antidepressant and an antianxiety agent.

The benzylamine derivatives and their salts according to the present invention show, also when orally administered, an anti-depression and anti-anxiety activity, an effect for activating the central nervous system, an effect for ameliorating disturbance of consciousness and a sigma receptor-agonistic action.

In the present complex society, a large number of people are suffering from mental disorders (e.g. obsessive-compulsive neurosis) caused by environmental stresses. The present compounds are useful as a remedy for obsessive-compulsive neurosis.

DETAILED DESCRIPTION OF PREFERRED EMBODIMENTS

The groups used in the benzylamine derivatives represented by general formula (1) and their salts according to the present invention are specifically as follows.

The lower alkyl group represented by R$^1$ includes straight-chain or branched-chain alkyl groups of 1–6 carbon atoms, such as methyl, ethyl, propyl, isopropyl, butyl, tert-butyl, pentyl, hexyl and the like.

The cycloalkyl group represented by $R^2$ can be exemplified by cycloalkyl groups of 3–8 carbon atoms, such as cyclopropyl, cyclopentyl, cyclobutyl, cyclohexyl, cycloheptyl, cyclooctyl and the like.

The halogen atom represented by $R^3$ includes a fluorine atom, a chlorine atom, a bromine atom, an iodine atom, etc.

Of the compounds of the present invention, preferable are compounds wherein $R^1$ is a methyl group or an ethyl group, $R^2$ is a cyclopropyl group, or a cyclobutyl group, and $R^3$ is a chlorine atom. Particularly preferable are compounds wherein $R^1$ is a methyl group, $R^2$ is a cyclopropyl group, and $R^3$ is a chlorine atom.

The benzylamine derivatives represented by general formula (1) according to the present invention can be produced by various processes. Preferable examples of the processes are shown below.

[Reaction formula-1]

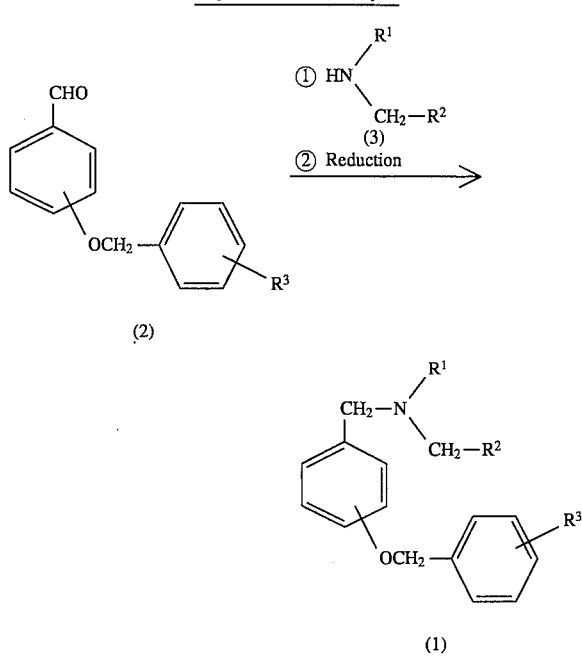

wherein $R^1$, $R^2$ and $R^3$ are the same as defined above.

In the Reaction formula-1, the reaction of the compound (2) with the compound (3) is conducted in the absence of any solvent or in the presence of an appropriate solvent, in the presence or absence of a dehydrating agent. The solvent includes, for example, alcohols such as methanol, ethanol, isopropanol and the like; aromatic hydrocarbons such as benzene, toluene, xylene and the like; halogenated hydrocarbons such as dichloromethane, dichloroethane, chloroform, carbon tetrachloride and the like; aprotic polar solvents such as dimethylformamide, dimethylacetamide, N-methyl-pyrrolidone and the like; and mixed solvents thereof. As the dehydrating agent, there are mentioned, for example, desiccants ordinarily used in dehydration of solvents, such as molecular sieve and the like; mineral acids such as hydrochloric acid, sulfuric acid, boron trifluoride and the like; and organic acids such as p-toluenesulfonic acid and the like. The reaction is conducted generally at about room temperature to 150° C., preferably at about room temperature to 100° C., and is complete generally in about 5 minutes to 10 hours. The amount of the compound of general formula (3) used is not particularly restricted but is generally at least equimolar to the compound of general formula (2), preferably 1–2 moles per mole of the compound (2). The amount of the dehydrating agent used is ordinarily a large excess when a desiccant is used, and is a catalysis amount when an acid is used. The thus obtained compound represented by the following general formula (A):

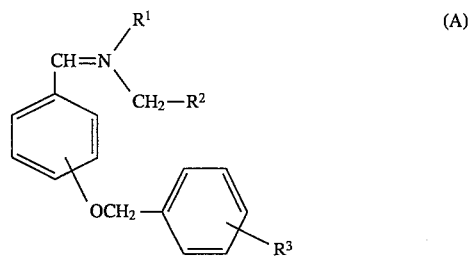

(wherein $R^1$, $R^2$ and $R^3$ are the same as defined above) is subjected to a reduction reaction without being isolated.

In the reduction reaction for the compound of general formula (A), various processes can be used. There can be used, for example, the same conditions as used in the catalytic hydrogenation (mentioned later) of compound of general formula (9). Preferably used, however, is a reduction process using a hydride reducing agent. This hydride reducing agent includes, for example, lithium aluminum hydride, sodium borohydride and diborane. It is used in an amount of at least 1 mole, preferably 1–10 moles per mole of the compound (2). This reduction reaction is conducted ordinarily in an appropriate solvent such as water, lower alcohol (e.g. methanol, ethanol or isopropanol), ether (e.g. tetrahydrofuran, diethyl ether or diglyme) or the like, generally at about −60 to 50° C., preferably −30° C. to room temperature for about 10 minutes to 5 hours. When lithium aluminum hydride or diborane is used as the reducing agent, it is preferable to use an anhydrous solvent such as diethyl ether, tetrahydrofuran, diglyme or the like.

[Reaction formula-2]

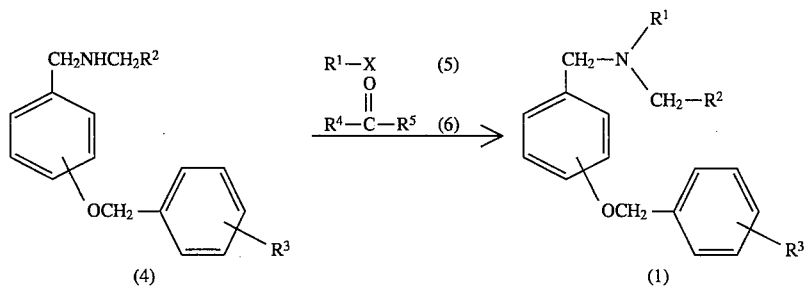

-continued
[Reaction formula-2]

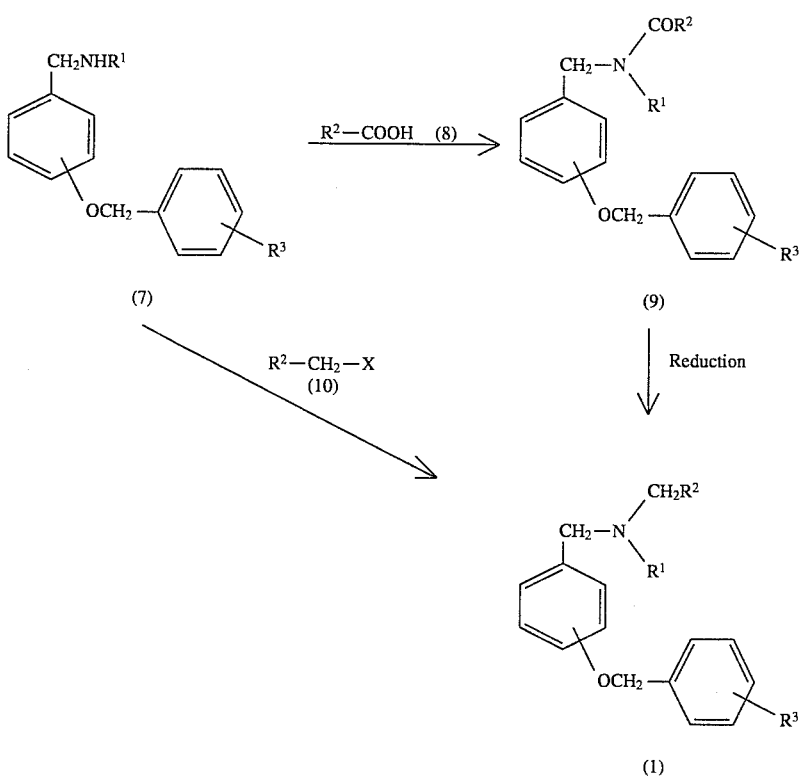

wherein $R^1$, $R^2$ and $R^3$ are the same as defined above; X is a halogen atom; and $R^4$ and $R^5$ are independently a hydrogen atom or a lower alkyl group.

The reaction of the compound (4) with the compound (5) and the reaction of the compound (7) with the compound (10) are conducted generally in an appropriate inert solvent in the presence or absence of a basic compound. As to the inert solvent, there can be mentioned, for example, aromatic hydrocarbons such as benzene, toluene, xylene and the like; ethers such as tetrahydrofuran, dioxane, diethylene glycol dimethyl ether and the like; lower alcohols such as methanol, ethanol, isopropanol, butanol and the like; acetic acid; ethyl acetate; acetone; acetonitrile; dimethyl sulfoxide; dimethylformamide; hexamethylphosphoric triamide; and mixed solvents thereof. As to the basic compound, there can be mentioned, for example, carbonates such as sodium carbonate, potassium carbonate, sodium hydrogencarbonate, potassium hydrogencarbonate and the like; metal hydroxides such as sodium hydroxide, potassium hydroxide and the like; sodium hydride; potassium; sodium; sodium amide; metal alcholates such as sodium methylate, sodium ethylate and the like; and organic bases such as pyridine, N-ethyldiisopropylamine, dimethylaminopyridine, triethylamine, 1,5-diazabicyclo[4.3.0]nonene-5 (DBN), 1,8-diazabicyclo [5.4.0]undecene-7 (DBU), 1,4-diazabicyclo[2.2.2]octane (DABCO) and the like. The proportions of the compound (4) and the compound (5), or the proportions of the compound (7) and the compound (10) are not particularly restricted and can be appropriately selected in wide ranges; however, the latter is used desirably in an amount of at least about 1 mole, preferably about 1–5 moles per mole of the former. The reaction is conducted generally at about 0°–200° C., preferably at about 0°–170° C. and is complete generally in about 30 minutes to 30 hours. Incidentally, an alkali metal halide (e.g. sodium iodide or potassium iodide), etc. may be added to the reaction system.

The reaction of the compound (4) with the compound (6) is conducted in the absence of any solvent or in the presence of an appropriate solvent, in the presence of a reducing agent. The solvent can be exemplified by water; alcohols such as methanol., ethanol, isopropanol and the like; acetonitrile; formic acid; acetic acid; ethers such as dioxane, diethyl ether, diglyme, tetrahydrofuran and the like; aromatic hydrocarbons such as benzene, toluene, xylene and the like; and mixed solvents thereof. The reducing agent can be exemplified by formic acid; alkali metal salts of fatty acids, such as sodium formate and the like; hydride reducing agents such as sodium borohydride, sodium cyanoborohydride, lithium aluminum hydride and the like; and catalytic reducing agents such as palladium black, palladium-carbon, platinum oxide, platinum black, Raney nickel and the like.

When formic acid is used as the reducing agent, the reaction is desirably conducted generally at about room temperature to 200° C., preferably at about 50°–150° C. and is complete in about 1–10 hours. The desirable amount of formic acid used is a large excess over the compound (4).

When a hydride reducing agent is used, the reaction is desirably conducted generally at about −30° to 100° C., preferably at about 0°–70° C. and is complete in about 30 minutes to 15 hours. The desirable amount of the reducing agent used is generally about 1–20 moles, preferably about 1–6 moles per mole of the compound (4). When, in particular, lithium aluminum hydride is used as the hydride reducing agent, there is preferably used, as the solvent, an ether (e.g. diethyl ether, dioxane, tetrahydrofuran or diglyme) or an aromatic hydrocarbon (e.g. benzene, toluene or xylene).

When a catalytic reducing agent is used, the reaction is desirably conducted in a hydrogen atmosphere of generally about normal pressure to 20 atm., preferably about normal pressure to 10 atm. in the presence of a hydrogen donor such as formic acid, ammonium formate, cyclohexene, hydrazine hydrate or the like generally at about −30° to 100° C., preferably at about 0°–60° C., and is complete generally in about 1–12 hours. The desirable amount of the catalytic reducing agent used is generally about 0.1–40% by weight, preferably about 1–20% by weight based on the compound (4).

The desirable amount of the compound (6) used is generally at least equimolar, preferably equimolar to a large excess to the compound (4).

The reaction of the compound (7) with the compound (8) is carried out in accordance with an ordinary amide-bond formation reaction. The amide-bond formation reaction can be carried out by various known processes, for example, (a) a mixed acid anhydride process which comprises, for example, reacting the carboxylic acid (8) with an alkyl halocarboxylate to form a mixed acid anhydride and reacting the anhydride with the amine (7); (b) an active ester process which comprises, for example, converting the carboxylic acid (8) into an active ester such as p-nitrophenyl ester, N-hydroxysuccinimide ester, 1-hydroxybenzotriazole ester or the like and reacting the active ester with the amine (7); (c) a carbodiimide process which comprises subjecting the carboxylic acid (8) and the amine (7) to a condensation reaction in the presence of an activating agent such as dicyclohexylcarbodiimide, carbonyldiimidazole or the like; and (d) other processes. The other processes (d) include, for example, a process which comprises converting the carboxylic acid (8) into a carboxylic acid anhydride with a dehydrating agent such as acetic anhydride or the like and reacting the carboxylic acid anhydride with the amine (7); a process which comprises reacting an ester of the carboxylic acid (8) and a lower alcohol with the amine (7); and a process which comprises reacting a halide of the carboxylic acid (8), i.e. a carboxylic acid halide with the amine (7). There may also be employed, for example, a process which comprises activating the carboxylic acid (8) with a phosphorus compound such as triphenylphosphine, diethyl chlorophosphate or the like and reacting the resulting compound with the amine (7), and a process which comprises converting the carboxylic acid (8) into an N-carboxyaminoacid anhydride with phosgene, trichloromethyl chloroformate or the like and reacting the anhydride with the amine (7). There may further be employed, for example, a process which comprises activating the carboxylic acid (8) with an acetylene compound such as trimethylsilylethoxyacetylene or the like and reacting the activation product with the amine (7).

In the mixed acid anhydride process (a), the mixed acid anhydride used can be obtained by an ordinary Schotten-Baumann reaction. The anhydride is reacted with the amine (7) generally without being isolated, whereby a compound of general formula (9) can be produced. The Schotten-Baumann reaction is conducted in the presence of a basic compound. The basic compound is a compound conventionally used in the Schotten-Baumann reaction and includes, for example, organic bases such as triethylamine, trimethylamine, pyridine, N,N-dimethylaniline, N-methylmorpholine, 4-dimethylaminopyridine, DBN, DBU, DABCO and the like, and inorganic bases such as potassium carbonate, sodium carbonate, potassium hydrogencarbonate, sodium hydrogencarbonate and the like. The reaction is conducted at about −20° to 100° C., preferably at 0°–50° C. for about 5 minutes to 10 hours, preferably about 5 minutes to 2 hours. The reaction of the resulting mixed acid anhydride with the amine (7) is conducted at about −20° to 150° C. preferably at 10°–50° C. for about 5 minutes to 10 hours, preferably about 5 minutes to 5 hours. The mixed acid anhydride process (a) is conducted in an appropriate solvent or in the absence of any solvent. The solvent may be any solvent conventionally used in the mixed acid anhydride process, and can be exemplified by halogenated hydrocarbons such as methylene chloride, chloroform, dichloroethane and the like; aromatic hydrocarbons such as benzene, toluene, xylene and the like; ethers such as diethyl ether, dioxane, diisopropyl ether, tetrahydrofuran, dimethoxyethane and the like; esters such as methyl acetate, ethyl acetate and the like; and aprotic polar solvents such as 1,1,3,3-tetramethylurea, N,N-dimethylformamide, dimethyl sulfoxide, hexamethylphosphoric triamide and the like and mixed solvent thereof. The alkyl halocarboxylate used in the mixed acid anhydride process (a) can be exemplified by methyl chloroformate, methyl bromoformate, ethyl chloroformate, ethyl bromoformate and isobutyl chloroformate. The alkyl halocarboxylate is used in an amount of generally at least 1 mole, preferably about 1–1.5 moles per mole of the amine (7). The carboxylic acid (8) is used in an amount of generally at least 1 mole, preferably about 1–1.5 moles per mole of the amine (7).

The active ester process (b), when, for example, N-hydroxysuccinimide ester is used, is conducted in an appropriate solvent which does not adversely affect the reaction, in the presence or absence of a basic compound. Into the reaction system may be added a condensation agent such as dicyclohexylcarbodiimide, carbonyldiimidazole, 1-ethyl-3-(3'-dimethylaminopropyl)carbodiimide or the like. As the basic compound, there can be used any of the basic compounds used in the above-mentioned Schotten-Baumann reaction; and there may further be used alkali metal salts of carboxylic acids (e.g. sodium acetate, sodium benzoate, sodium formate, potassium acetate, lithium benzoate and cesium acetate), alkali metal halides (eg. potassium fluoride and cesium fluoride), etc. Specific examples of the solvent are halogenated hydrocarbons such as methylene chloride, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N-dimethylformamide, dimethyl sulfoxide, hexamethylphosphoric triamide and the like; and mixed solvents thereof. The reaction is conducted at 0°–150° C., preferably at 10°–100° C. and is complete in 5–30 hours. The desirable amount of the N-hydroxysuccinimide ester used is generally at least 1 mole, preferably 1–2 moles per mole of the amine (7).

A compound (9) can also be obtained by reacting the amine (7) with the carboxylic acid (8) in the presence of a phosphorus compound as condensation agent, such as triphenylphosphine, triphenylphosphine2,2'-dipyridyl disulfide, diethyl chlorophosphate, diphenylphosphinyl chloride, phenyl N-phenylphosphoramide chloridate, diethyl cyanophosphate, bis(2-oxo-3-oxazolidinyl)phosphinic chloride or the like. As the basic compound, there can widely be used known basic compounds, for example, the basic compounds used in the above-mentioned Schotten-Baumann reaction, sodium hydroxide and potassium hydroxide. The solvent used includes, for example, the solvents used in the mixed acid anhydride process (a), pyridine, acetone, acetonitrile and mixed solvents of two or more of said solvents. The reaction is conducted generally at about −20° to 150° C., preferably at about 0°–100° C. and is complete generally in 5 minutes to 30 hours. The desirable amounts of the condensation agent and the carboxylic acid (8) used are independently at least about 1 mole, preferably about 1–2 moles per mole of the amine (7).

A compound (9) can also be obtained by reacting the amine (7) with the carboxylic acid (8) in the presence of a condensation agent. The reaction is conducted in an appropriate solvent in the presence or absence of a catalyst. The solvent can be exemplified by halogenated hydrocarbons such as dichloromethane, dichloroethane, chloroform, carbon tetrachloride and the like; acetonitrile; and dimethylformamide. The catalyst can be exemplified by organic bases such as dimethylaminopyridine, 4-piperidinopyridine and the like; salts such as pyridinium tosylate and the like; camphorsulfonic acid; and mercury oxide. The condensation agent includes, for example, acetylene compounds such as trimethylsilylethoxyacetylene and the like. The condensation agent is desirably used in an amount of generally 1–10 moles, preferably 2–6 moles per mole of the amine (7). The carboxylic acid (8) is desirably used in an amount of generally at least about 1 mole, preferably about 1–2 moles per mole of the amine (7). The reaction is conducted generally at about 0°–150° C., preferably at about room temperature to 100° C. and is complete generally in about 1–10 hours.

When there is used one of the processes (d) which comprises reacting a halide of the carboxylic acid (8), i.e. a carboxylic acid halide with the amine (7), the reaction is conducted in an appropriate solvent in the presence of a dehydrohalogenating agent. An ordinary basic compound is used as the dehydrohalogenating agent. The basic compound can be selected widely from known basic compounds and includes, for example, the basic compounds used in the Schotten-Baumann reaction, sodium hydroxide, potassium hydroxide, sodium hydride and potassium hydride. The solvent includes the solvents used in the mixed acid anhydride process (a); alcohols such as methanol, ethanol, propanol, butanol, 3-methoxy-1-butanol, ethyl cellosolve, methyl cellosolve and the like; pyridine; acetone; acetonitrile; mixed solvents of two or more of said solvents; and so forth. The proportions of the amine (7) and the carboxylic acid halide are not particularly restricted and can be selected appropriately in wide ranges, but the latter is desirably used in an amount of generally at least about 1 mole, preferably about 1–5 moles per mole of the former. The reaction is conducted generally at about −20° to 180° C., preferably at about 0°–150° C. and is complete generally in about 5 minutes to 30 hours.

In the above, the carboxylic acid halide can be produced, for example, by reacting the carboxylic acid (8) with a halogenating agent in the presence or absence of a solvent. The solvent can be any solvent which does not adversely affect the reaction, and includes, for example, aromatic hydrocarbons such as benzene, toluene, xylene and the like; halogenated hydrocarbons such as chloroform, methylene chloride, carbon tetrachloride and the like; ethers such as dioxane, tetrahydrofuran, diethyl ether and the like; dimethylformamide; and dimethyl sulfoxide. The halogenating agent can be an ordinary halogenating agent capable of converting the hydroxyl group of carboxyl group into a halogen, and can be exemplified by thionyl chloride, phosphorus oxychloride, phosphorus oxybromide, phosphorus pentachloride and phosphorus pentabromide. The proportions of the carboxylic acid (8) and the halogenating agent used are not particularly restricted and can be selected appropriately; however, when the reaction is conducted in the absence of any solvent, the latter is used generally in large excess of the former and, when the reaction is used in a solvent, the latter is used in an amount of generally at least about 1 mole, preferably 2–4 moles per mole of the former. The reaction temperature and time are not particularly restricted, either, but are generally about room temperature to 100° C., preferably 50°–80° C. and about 30 minutes to 6 hours, respectively.

The reaction for converting the compound (9) into a compound (1) can be conducted by various processes. It can be conducted, for example, by (1) subjecting the compound (9) to catalytic hydrogenation in an appropriate solvent in the presence of a catalyst. The solvent includes, for example, water; acetic acid; alcohols such as methanol, ethanol, isopropanol and the like; hydrocarbons such as hexane, cyclohexane and the like; ethers such as diethylene glycol dimethyl ether, dioxane, tetrahydrofuran, diethyl ether and the like; esters such as ethyl acetate, methyl acetate and the like; aprotic polar solvents such as dimethylformamide and the like; and mixed solvents thereof. As the catalyst, there can be used, for example, palladium, palladium black, palladium-carbon, platinum, platinum oxide, copper chromite and Raney nickel. The desirable amount of the catalyst used is generally about 0.02–1 time the amount of the compound (9). The reaction temperature is generally about −20° to 100° C., preferably about 0°–70° C.; the desirable hydrogen pressure is generally 1–10 atm.; and the reaction is complete generally in about 0.5–20 hours.

In the reaction for converting the compound (9) into a compound (1), there is preferably used (2) a reduction process using a hydride reducing agent. The hydride reducing agent includes, for example, lithium aluminum hydride, sodium borohydride and diborane. It is used in an amount of generally at least 1 mole, preferably 1–10 moles per mole of the compound (9). The reduction reaction is conducted generally in an appropriate solvent such as water, lower alcohol (e.g. methanol, ethanol or isopropanol), ether (e.g. tetrahydrofuran, diethyl ether or diglyme), acetic acid or the like, generally at about 0°–200° C., preferably at 0–°170° C. for about 10 minutes to 10 hours. When lithium aluminum hydride or diborane is used as the reducing agent, it is preferable to use an anhydrous solvent such as diethyl ether, tetrahydrofuran, diglyme or the like.

[Reaction formula-3]

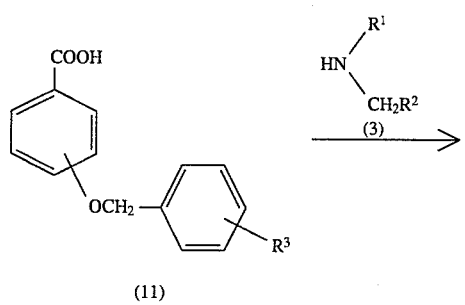

-continued
[Reaction formula-3]

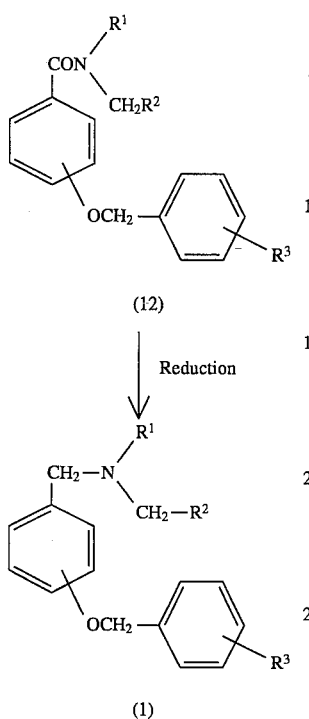

wherein $R^1$, $R^2$ and $R^3$ are the same as defined above.

The reaction of the carboxylic acid compound (11) with the amine compound (3) can be conducted under the same conditions as in the reaction of the amine compound (7) with the carboxylic acid compound (8) in the Reaction formula-2. The desirable amount of the amine compound (3) used is determined per molar quantity of the carboxylic compound (11).

The reduction reaction for the compound (12) can be conducted under the same conditions as in the reduction reaction for the compound (9) in the Reaction formula-2. The compound (12) can be produced, for example, by a process shown by the following Reaction formula-4.

[Reaction formula-4]

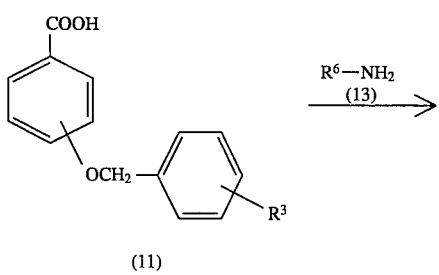

-continued
[Reaction formula-4]

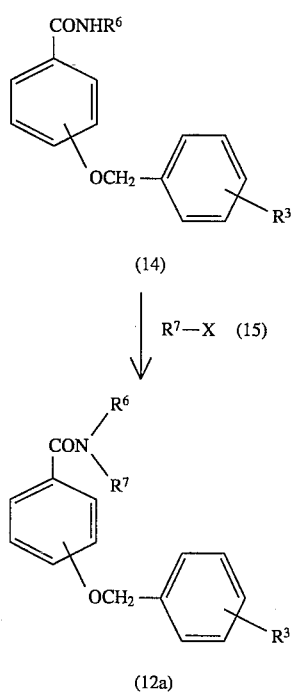

wherein $R^3$ and X are the same as defined above; and $R^6$ and $R^7$ are each $R^1$ or $-CH_2R^2$ ($R^1$ and $R^2$ are the same as defined above) with a proviso that when $R^6$ is $R^1$, $R^7$ is $-CH_2R^2$ and, when $R^6$ is $-CH^2R^2$, $R^7$ is $R^1$.

The reaction of the compound (11) with the compound (13) is conducted under the same conditions as in the reaction of the compound (11) with the compound (3) in the Reaction formula-3. The reaction of the compound (14) with the compound (15) is conducted under the same conditions as in the reaction of the compound (4) with the compound (5) in the Reaction formula-2.

The starting material (4) or (7) in the Reaction formula-2 can be produced, for example, by a process shown by the following Reaction formula-5.

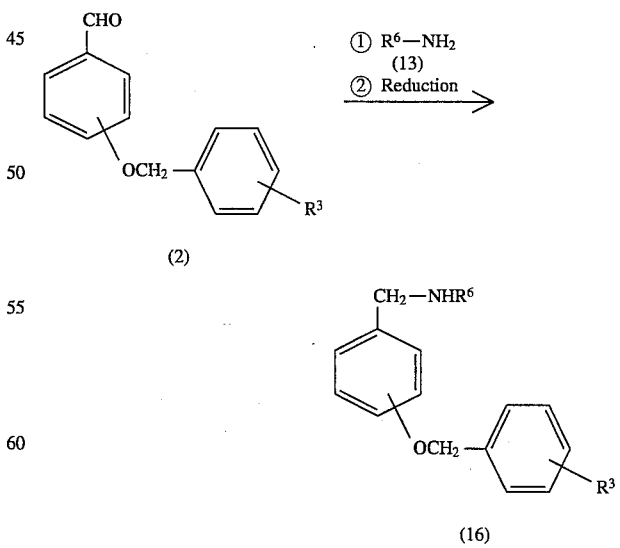

wherein $R^3$ and $R^6$ are the same as defined above.

In the Reaction formula-5, a compound (16) wherein $R^6$ is $R^1$, is the compound (7), and a compound (16) wherein $R^6$ is —$CH_2R^2$, is the compound (4). The reaction of the compound (2) with the compound (13) is conducted under the same conditions as in the reaction of the compound (2) with the compound (3) in the Reaction formula-1.

The starting material (2) in the Reaction formula-1 and the starting material (11) in the Reaction formula-3 or the Reaction formula-4 can be produced, for example, by a process shown by the following Reaction formula-6.

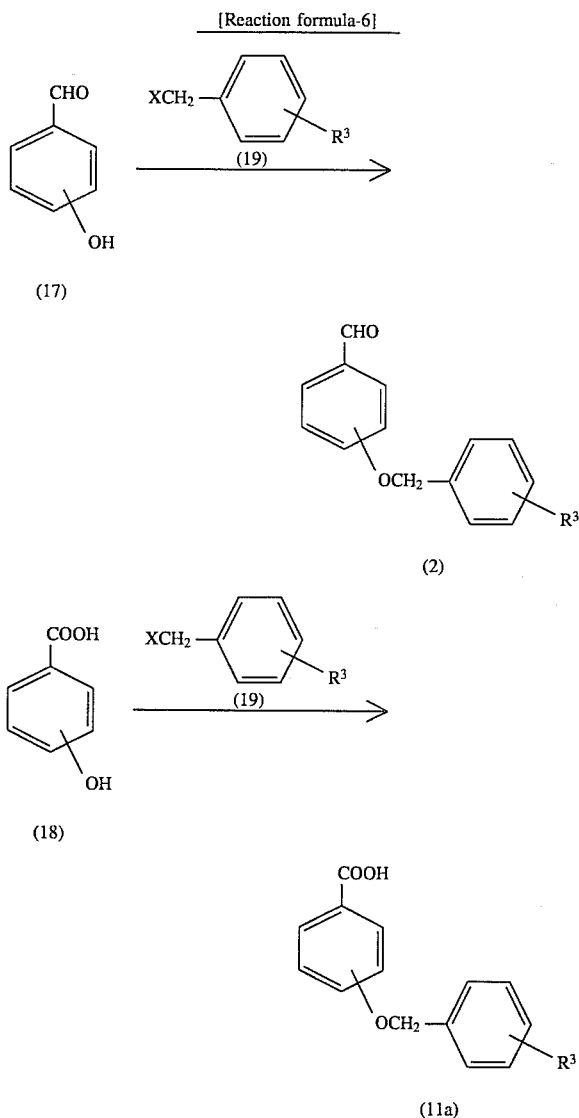

wherein $R^3$ and X are the same as defined above.

The reaction of the compound (17) with the compound (19) and the reaction of the compound (18) with the compound (19) are each conducted under the same conditions as in the reaction of the compound (4) with the compound (5) in the Reaction formula-2.

Of the present compounds represented by general formula (1), those having a basic group can each form an acid addition salt easily by being reacted with a pharmacologically acceptable acid. The acid can be exemplified by inorganic acids such as hydrochloric acid, sulfuric acid, phosphoric acid, hydrobromic acid and the like, and organic acids such as oxalic acid, acetic acid, succinic acid, malonic acid, methanesulfonic acid, maleic acid, fumaric acid, malic acid, tartaric acid, citric acid, benzoic acid and the like.

Each of the intended compounds obtained by the above reaction formulas can be easily isolated and purified by ordinary separation means. The separation means can be exemplified by solvent extraction, dilution, recrystallization, column chromatography and preparative thin-layer chromatography.

Each of the compounds of general formula (1) is used generally in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be prepared in various forms depending upon the purpose of remedy, and the typical forms include tablets, pills, a powder, a solution, a suspension, an emulsion, granules, capsules, suppositories, an injection (e.g. solution or suspension), etc. In preparing tablets, there can be used various carriers known in the field, exemplified by excipients such as lactose, white sugar, sodium chloride, glucose, urea, starch, calcium carbonate, kaolin, crystalline cellulose, silicic acid and the like; binders such as water, ethanol, propanol, simple syrup, lactose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, there can be used various carriers known in the field, exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, there can be used various carriers known in the field, exemplified by a polyethylene glycol, cacao butter, a higher alcohol ester, gelatin and a semi-synthetic glyceride. In preparing an injection (solution, emulsion or suspension), the solution and suspension are sterilized and are preferably made isotonic to the blood. In preparing the solution, emulsion or suspension, there can be used all diluents conventionally used in the field, such as water, ethyl alcohol, propylene glycol, ethoxylated isostearyl alcohol, polyoxyisostearyl alcohol and polyoxyethylene sorbitan-fatty acid esters. In this case, the pharmaceutical preparation may contain sodium chloride, glucose or glycerine in an amount sufficient to make the preparation isotonic, and may further contain a solubilizing agent, a buffer solution, a soothing agent, etc. all ordinarily used. The pharmaceutical preparation may furthermore contain, as necessary, a coloring agent, a preservative, a perfume, a flavoring agent, a sweetening agent and other drugs.

The amount of the compound of general formula (1) or its salt according to the present invention to be contained in the pharmaceutical preparation is not particularly restricted and can be appropriately selected from a wide range, but the desirable amount is generally 1–70% by weight in the pharmaceutical preparation.

The method for administering the pharmaceutical preparation is not particularly restricted. It is decided depending upon the form of preparation, the age, distinction of sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation is appropriately selected depending upon the administration method, the age, distinction of sex and other conditions of patient, the disease condition of patient, etc., but the desirable dose is generally about 0.2–200 mg per kg of body weight per day in terms of the amount of the active ingredient, i.e. the compound of general formula (1) or its salt.

Description is made hereinafter on Preparation Examples, Reference Examples, Examples and Results of Pharmacological Tests.

Preparation Example 1

| | |
|---|---|
| 4-(4-Chlorobenzyloxy)-N-cyclopropyl-methyl-N-methylbenzylamine | 5 mg |
| Starch | 132 mg |
| Magnesium stearate | 18 mg |
| Lactose | 45 mg |
| Total | 200 mg |

Tablets each containing the above composition were produced by an ordinary method.

Preparation Example 2

| | |
|---|---|
| 2-(4-Chlorobenzyloxy)-N-cyclopropyl-methyl-N-methylbenzylamine | 150 mg |
| Avicel (trade mark, a product of ASAHI CHEMICAL INDUSTRY CO., LTD.) | 40 g |
| Corn starch | 30 g |
| Magnesium stearate | 2 g |
| Hydroxypropyl methyl cellulose | 10 g |
| Polyethylene glycol 6000 | 3 g |
| Castor oil | 40 g |
| Methanol | 40 g |

The present invention compound, Avicel, corn starch and magnesium stearate were mixed and ground, and then made into tablets using a punch (R: 10 mm). The tablets were coated with a film coating agent consisting of hydroxypropyl methyl cellulose, polyethylene glycol 6000, castor oil and methanol, whereby film-coated tablets were produced.

Reference Example 1

To a solution of 1.2 g of 3-hydroxybenzaldehyde in 50 ml of N,N-dimethylformamide were added 2.4 g of 4-chlorobenzyl chloride and 2.1 g of potassium carbonate. The mixture was stirred at 60° C. for 3 hours. After cooling, the reaction mixture was treated with ethyl acetate-water. The resulting ethyl acetate layer was separated, washed with water, dried with anhydrous magnesium sulfate, and subjected to vacuum distillation to remove the solvent. The resulting residue was purified by silica gel column chromatography (eluant: n-hexane/ethyl acetate=102) to obtain 1.9 g of 3-(4-chlorobenzyloxy)benzaldehyde.

Colorless needles $^1$H-NMR (CDCl$_3$) δ ppm: 5.10 (2H, s), 7.21–7.25 (1H, m), 7.38 (4H, s), 7.43–7.49 (3H, m), 9.98 (1H, s)

Reference Example 2

To a solution of 10 g of 4-hydroxybenzoic acid in 100 ml of N,N-dimethylformamide were added 29.1 g of 4-chlorobenzyl chloride and 25 g of potassium carbonate. The mixture was stirred at 60° C. for 3 hours. After cooling, the reaction mixture was treated with ethyl acetate-water. The resulting ethyl acetate layer was separated, washed with water, dried with anhydrous magnesium sulfate, and subjected to vacuum distillation to remove the solvent. The resulting residue was washed with n-hexane, then collected by filtration, and suspended in 50 ml of ethanol. To the suspension was added 100 ml of a 2N aqueous sodium hydroxide solution. The mixture was stirred at room temperature for 4 days and then neutralized with concentrated hydrochloric acid. The resulting crystals were collected by filtration and recrystallized from chloroform to obtain 16.7 g of 4-(4-chlorobenzyloxy)benzoic acid.

Colorless scales $^1$H-NMR (DMSO-d$_6$) δ ppm: 5.14 (2H, s), 6.95 (2H, d, J=8.5 Hz), 7.47 (2H, d, J=11 Hz), 7.52 (2H, d, J=11 Hz), 7.87 (2H, d, J=8.5 Hz)

Reference Example 3

2-(4-Chlorobenzyloxy)benzoic acid was obtained in the same manner as in Reference Example 2 by using 2-hydroxybenzoic acid as a starting material.

Yellow prisms $^1$H-NMR (CDCl$_3$) δ ppm: 5.26 (2H, s), 7.07–7.17 (2H, m), 7.39 (4H, s), 7.51–7.58 (1H, m), 8.16 (1H, dd, J=2.0 Hz, J=8.0 Hz)

Reference Example 4

The following compounds were obtained in the same manner as in Reference Example 1 by using 3-hydroxybenzaldehyde as a starting material.

3-(2-Chlorobenzyloxy)benzaldehyde
Colorless granules
$^1$H-NMR (CDCl$_3$) δ ppm: 5.21 (2H, s), 7.24–7.31 (3H, m), 7.39–7.57 (5H, m), 9.98 (1H, s)

3-(3-Chlorobenzyloxy)benzaldehyde
Colorless oil
$^1$H-NMR (CDCl$_3$) δ ppm: 5.10 (2H, s), 7.22–7.33 (4H, m), 7.43–7.52 (4H, m), 9.98 (1H, s)

3-(4-Fluorobenzyloxy)benzaldehyde
Pink powder
$^1$H-NMR (CDCl$_3$) δ ppm: 5.08 (2H, s), 7.09 (2H, dd, J=8.5 Hz, J=8.5 Hz), 7.22–7.26 (1H, m), 7.39–7.50 (5H, m), 9.98 (1H, s)

3-(4-Bromobenzyloxy)benzaldehyde
White powder
$^1$H-NMR (CDCl$_3$) δ ppm: 5.07 (2H, s), 7.20–7.26 (1H, m), 7.30–7.34 (2H, m), 7.42–7.55 (5H, m), 9.97 (1H, s)

Reference Example 5

A solution of 62 g of 3-(4-chlorobenzyloxy)-benzaldehyde and 20 g of cyclopropylmethylamine in 750 ml of methanol was stirred at room temperature for 15 minutes. Thereto was slowly added 12 g of sodium borohydride with ice-cooling. The resulting mixture was stirred at the same temperature for 1 hour. The reaction mixture was dissolved in 1 liter of chloroform. The solution was washed with water, dried with anhydrous magnesium sulfate, and subjected to vacuum distillation to remove the solvent, whereby 81 g of 3-(4-chlorobenzyloxy)-N-cyclopropylmethylbenzylamine was obtained.

Yellow oil $^1$H-NMR (CDCl$_3$) δ ppm: 0.06–0.12 (2H, m), 0.44–0.51 (2H, m), 0.92–1.00 (1H, m), 1.55 (1H, m), 2.47 (2H, d, J=7 Hz), 3.79 (2H, s), 5.04 (2H, s), 6.81–6.96 (3H, m), 7.24 (1H, dd, J=8 Hz, J=8 Hz), 7.36 (4H, s)

Reference Example 6

3-(4-Chlorobenzyloxy)-N-methylbenzylamine was obtained in the same manner as in Reference Example 5 by using suitable starting materials.

Yellow oil 1H-NMR (CDCl$_3$) δ ppm: 1.40 (1H, bs), 2.45 (3H, s), 3.73 (2H, s), 5.03 (2H, s), 6.82–6.95 (3H, m), 7.24 (1H, dd, J=8.0 Hz, J=8.0 Hz), 7.36 (4H, s)

Reference Example 7

To a solution of 2.1 g of 3-(4-chlorobenzyloxy)-N-methylbenzylamine and 3.4 ml of triethylamnine in 50 ml of dichloromethane was dropwise added 1.0 ml of cyclobutanecarbonyl chloride with ice-cooling. The mixture was stirred at room temperature for 1 hour. The reaction mixture was washed with water, dried with anhydrous magnesium sulfate, and subjected to vacuum distillation to remove the solvent, whereby 3.1 g of 3 -(4-chlorobenzyloxy)-N-cyclobutonecarbonyl-N-methylbenzylamine was obtained.

Yellow oil $^1$H-NMR (CDCl$_3$) δ ppm: 1.81–2.53 (6H, m), 2.80, 2.90 (total 3H, s), 3.20–3.48 (1H, m), 4.40, 4.54 (total 2H, s), 5.01 (2H, s), 6.70–6.93 (3H, m), 7.19–7.33 (1H, m), 7.35 (4H, s)

Reference Example 8

In 80 ml of thionyl chloride was dissolved 5 g of 4-(4-chlorobenzyloxy)benzoic acid. The solution was refluxed with heating, for 1 hour and then subjected to vacuum distillation to remove thionyl chloride. The resulting residue was dissolved in 30 ml of dichloromethane. The solution was dropwise added, with ice-cooling, to a solution of 2.2 g of cyclopropylmethylamine and 10 ml of triethylamine in 100 ml of dichloromethane. The mixture was stirred at room temperature for 1 hour. The reaction mixture was washed with 2N hydochloric acid and water, dried with anhydrous magnesium sulfate, and subjected to distillation to remove the solvent, whereby 4.2 g of 4-(4 -chlorobenzyloxy)-N-cyclopropylmethylbenzamide was obtained.

White powder $^1$H-NMR (CDCl$_3$) δ ppm: 0.23–0.30 (2H, m), 0.51–0.59 (2H, m), 1.00–1.15 (1H, m), 3.30 (2H, dd, J=5.5 Hz, J=7.0 Hz), 5.07 (2H, s), 6.09–6.21 (1H, m), 6.95–7.00 (2H, m), 7.36 (4H, s), 7.72–7.77 (2H, m)

Reference Example 9

2-(4-Chlorobenzyloxy)-N-cyclopropylmethylbenzamide was obtained in the same manner as in Reference Example 8 by using 2-(4-chlorobenzyloxy)benzoic acid as a starting material.

White powder $^1$H-NMR (CDCl$_3$) δ ppm: 0.02–0.08 (2H, m), 0.29–0.37 (2H, m), 0.77–0.85 (1H, m), 3.22 (2H, dd, J=5.0 Hz, J=7.0 Hz), 5.14 (2H, s), 7.03–7.15 (2H, m), 7.38–7.48 (1H, m), 7.41 (4H, s), 7.72–7.98 (1H, m), 8.24 (1H, dd, J=2.0 Hz, J=8.0 Hz)

Reference Example 10

In 30 ml of N,N-dimethylformamide was dissolved 1.5 g of 4-(4-chlorobenzyloxy)-N-cyclopropylmethylbenzamide. To the solution was added 0.25 g of sodium hydride. The mixture was stirred at room temperature for 30 minutes and then at 60° C. for 30 minutes. The reaction mixture was ice-cooled, and 0.5 ml of methyl iodide was added thereto. The mixture was stirred overnight at room temperature. The reaction mixture was treated with ethyl acetate-water. The resulting ethyl acetate layer was separated, washed with water, dried with anhydrous magnesium sulfate, and subjected to distillation to remove the solvent. The resulting residue was purified by column chromatography (eluant: dichloromethane/acetone=50/1) to obtain 1.4 g of 4-(4-chlorobenzyloxy)-N-cyclopropylmethyl-N-methylbenzamide.

Colorless oil $^1$H-NMR (CDCl$_3$) δ ppm: 0.00–0.40 (2H, m), 0.51–0.63 (2H, m), 0.88–1.11 (1H, m), 2.95–3.50 (5H, m), 5.05 (2H, s), 6.93–6.97 (2H, m), 7.26–7.40 (2H, m), 7.37 (4H, s)

Reference Example 11

2-(4-Chlorobenzyloxy)-N-cyclopropylmethyl-N-methylbenzamide was obtained in the same manner as in Reference Example 10 by using, as a starting material, 2-(4-chlorobenzyloxy)-N-cyclopropylmethylbenzamide.

Light yellow oil $^1$H-NMR (CDCl$_3$) δ ppm: 0.05–0.10, 0.23–0.37, 0.37–0.55 (total 4H, m), 0.75–0.92, 0.92–1.08 (total 1H, m), 2.88–3.25 (5H, m), 5.07–5.14 (2H, m), 6.89–7.14 (2H, m), 7.25–7.45 (6H, m)

Reference Example 12

The following compounds were obtained in the same manner as in Reference Example 5 by using suitable starting materials.

3-(2-Chlorobenzyloxy)-N-cyclopropylmethylbenzylamine

Colorless oil $^1$H-NMR (CDCl$_3$) δ ppm: 0.07–0.13 (2H, m), 0.44–0.51 (2H, m), 0.92–1.10 (1H, m), 1.35–1.61 (1H, m), 2.48 (2H, d, J=7.0 Hz), 3.80 (2H, s), 5.17 (2H, s), 6.85–6.99 (3H, m), 7.25–7.32 (3H, m), 7.38–7.42 (1H, m), 7.55–7.59 (1H, m)

(3-Chlorobenzyloxy)-N-cyclopropylmethylbenzylamine
Colorless oil $^1$H-NMR (CDCl$_3$) δ ppm: 0.07–0.12 (2H, m), 0.44–0.51 (2H, m), 0.50–1.08 (1H, m), 1.35–1.52 (1H, m), 2.48 (2H, d, J=7.0 Hz), 3.80 (2H, s), 5.04 (2H, s), 6.82–6.97 (3H,m), 7.21–7.30 (4H, m), 7.44–7.45 (1H, m)

3-(4-Fluorobenzyloxy)-N-cyclopropylmethylbenzylamine

Colorless oil $^1$H-NMR (CDCl$_3$) δ ppm: 0.07–0.13 (2H, m), 0.44–0.51 (2H, m), 0.92–1.08 (1H, m), 1.40–1.70 (1H, m), 2.47 ( 2H, d, J=7.0 Hz), 3.80 (2H, s), 5.03 (2H, s), 6.83–6.97 (3H, m), 7.04–7.10 (2H, m), 7.26 ( 1H, dd, J=8.0 Hz, J=8.0 Hz), 7.38–7.44 (2H, m)

3-(4-Bromobenzyloxy ) -N-cyclopropylmethylbenzylamine

Colorless oil $^1$H-NMR (CDCl$_3$) δ ppm: 0.06–0.12 (2H, m), 0.44–0.51 (2H, m), 0.91–1.06 (1H, m), 1.34–1.60 (1H, m), 2.47 (2H, d, J=7.0 Hz), 3.79 (2H, s), 5.02 (2H, s), 6.81–6.95 (3H, m), 7.20–7.33 (3H, m), 7.49–7.52 (2H, m)

Reference Example 13

The following compounds were obtained in the same manner as in Reference Example 8 by using suitable starting materials.

3-(4-Chlorobenzyloxy)-N-cyclohexylmethylbenzamide
White powder
$^1$H-NMR (CDCl$_3$) δ ppm: 0.95–1.11 (2H, m), 1.11–1.36 (3H, m), 1.56–1.90 (6H, m), 3.29 (2H, dd, J=6.5 Hz, J=6.5 Hz), 5.06 (2H, s), 6.18–6.29 (1H, m), 7.04–7.09 (1H, m), 7.26–7.43 (3H, m), 7.36 (4H, s)

3-(4-Chlorobenzyloxy)-N-cyclopropylmethyl-N-propylbenzamide
White powder
$^1$H-NMR (CDCl$_3$) δ ppm: 0.01–1.82 (10H, m), 3.00–3.63 (4H, m), 5.05 (2H, s), 6.91–6.99 (3H, m), 7.30 (1H, dd, J=8.0 Hz, J=8.0 Hz), 7.35 (4H, s)

Reference Example 14

3-(4-Chlorobenzyloxy)-N-cyclohexylmethyl-N-methylbenzamide was obtained in the same manner as in Reference Example 10 by using, as a starting material, 3-(4-chlorobenzyloxy)-N-cyclohexylmethylbenzamide.

Colorless oil $^1$H-NMR (CDCl$_3$) δ ppm: 0.55–0.72, 0.95–1.37, 1.52–1.85 (total 11H, m), 2.89, 3.04 (total 3H, s), 3.06, 3.37 (total 2H, s), 5.05 (2H, s), 6.92–6.99 (3H, m), 7.30 (1H, dd, J=8.5 Hz, J=8.5 Hz), 7.36 (4H, s)

EXAMPLE 1

In a mixture of 150 ml of formic acid and 150 ml of 37% formaldehyde was dissolved 80 g of 3-(4 -chlorobenzyloxy)-N-cyclopropylmethylbenzylamine. The solution was refluxed with heating, for 3 hours. The reaction mixture was cooled to room temperature, and 150 ml of concentrated hydrochloric acid was added thereto. The mixture was subjected to vacuum distillation to remove the solvent. The resulting residue was treated with chloroform-aqueous sodium hydroxide solution. The resulting chloroform layer was separated, washed with water, dried with anhydrous sodium sulfate, and subjected to vacuum distillation to remove the solvent, whereby 86 g of 3-(4-chlorobenzyloxy)-N-cyclopropylmethyl-N-methylbenzylamine was obtained as a brown oil.

Of 86 g, 3 g was converted into a hydrochloride. The hydrochloride was recrystallized from ethyl acetate to obtain 2.1 g of 3-(4-chlorobenzyloxy)-N-cyclopropylmethyl-N-methylbenzylamine hydrochloride.

Colorless needles

Melting point: 119.0°–121.0° C.

The compounds of Examples 2–10 shown in Table 1 were obtained in the same manner as in Example 1 by using suitable starting materials.

TABLE 1

| Example No. | R$^1$ | —CH$_2$—R$^2$ | —O—CH$_2$—(aryl)—R$^3$ | Crystal form (Recrystallization solvent) | Melting point (°C.) (Salt form) |
|---|---|---|---|---|---|
| 2 | —CH$_3$ | —CH$_2$—(cyclopropyl) | 4 —OCH$_2$—(phenyl)—Cl | White powder (Ethanol) | 154.0–154.5 (Oxalate) |
| 3 | —CH$_3$ | —CH$_2$—(cyclopropyl) | 2 —OCH$_2$—(phenyl)—Cl | Slightly blue powder (Etanol-diethyl ether) | 125.0–126.5 (Oxalate) |
| 4 | —CH$_3$ | —CH$_2$—(cyclobutyl) | 3 —OCH$_2$—(phenyl)—Cl | White powder (Ethanol) | 102.5–103.0 (Maleate) |

TABLE 1-continued

Structure:
CH₂—N(R¹)(CH₂—R²) attached to benzene ring with O—CH₂—(aryl-R³) substituent

| Example No. | R¹ | —CH₂—R² | —O—CH₂—(aryl-R³) | Crystal form (Recrystallization solvent) | Melting point (°C.) (Salt form) |
|---|---|---|---|---|---|
| 5 | —CH₃ | —CH₂-cyclopropyl | 3—OCH₂—C₆H₄—Cl | White powder (Ethanol) | 125.0–126.0 (Oxalate) |
| 6 | —CH₃ | —CH₂-cyclopropyl | 3—OCH₂—C₆H₄—Cl | White powder (Ethanol) | 140.5–141.0 (Oxalate) |
| 7 | —CH₃ | —CH₂-cyclopropyl | 3—OCH₂—C₆H₄—F | Colorless granules (Ethanol) | 138.0–139.0 (Oxalate) |
| 8 | —CH₃ | —CH₂-cyclopropyl | 3—OCH₂—C₆H₄—Br | White powder (Ethanol) | 129.0–141.0 (Oxalate) |
| 9 | —CH₃ | —CH₂-cyclohexyl | 3—OCH₂—C₆H₄—Cl | White powder (Ethanol) | 187.0–187.5 (Oxalate) |
| 10 | -n-C₃H₇ | —CH₂-cyclopropyl | 3—OCH₂—C₆H₄—Cl | White powder (Ethanol-diethyl ether) | 78.0–82.5 (Oxalate) |

EXAMPLE 11

0.5 g of lithium aluminum hydride was added to a solution of 1.4 g of 4-(4-chlorobenzyloxy)-N-cyclopropylmethyl-N-methylbenzamide in 50 ml of tetrahydrofuran. The mixture was refluxed with heating, for 3 hours. The reaction mixture was cooled, and 2 ml of water was added thereto. The mixture was stirred at room temperature for 14 hours. The reaction mixture was filtered and the filtrate was treated with water-diethyl ether. The resulting diethyl ether layer was separated, washed with water, dried with anhydrous magnesium sulfate, and subjected to vacuum distillation to remove the solvent. The resulting residue was converted into an oxalate. The oxalate was recrystallized from ethanol to obtain 1.3 g of 4-(4-chlorobenzyloxy)-N-cyclopropylmethyl-N-methylbenzylamine oxalate.

White powder

Melting point: 154.0°–154.5° C.

The compounds of Examples 1 and 3–10 were obtained in the same manner as in Example 11 by using suitable starting materials.

EXAMPLE 12

To a solution of 62 g of 4-(4-chlorobenzyloxy)benzaldehyde and 24 g of N-cyclopropylmethyl-N-methylamine in 750 ml of methanol was slowly added 12 g of sodium borohydride with ice-cooling. The mixture was stirred at the same temperature for 1 hour. The reaction mixture was dissolved in 1 liter of chloroform. The solution was washed with water, dried with anhydrous magnesium sulfate, and subjected to vacuum distillation to remove the solvent. The resulting residue was converted into an oxalate. The oxalate was recrystallized from ethanol to obtain 84 g of 4-(4-chlorobenzyloxy)-N-cyclopropylmethyl-N-methylbenzylamine oxalate.

White powder

Melting point: 154.0°–154.5° C.

The compounds of Examples 1 and 3–10 were obtained in the same manner as in Example 12 by using suitable starting materials.

EXAMPLE 13

0.92 g of lithium aluminum hydride was added to a solution of 2.8 g of 3-(4-chlorobenzyloxy)-N-cyclobutanecarbonyl-N-methylbenzylamine in 50 ml of tetrahydrofuran. The mixture was refluxed with heating, for 3 hours. The reaction mixture was cooled, and 2 ml of water was added thereto. The mixture was stirred for 14 hours and then filtered. The filtrate was treated with water-diethyl ether. The resulting diethyl ether layer was separated, washed with water, dried with anhydrous magnesium sulfate, and subjected to vacuum distillation to remove the solvent. The residue was converted into a maleate. The maleate was recrystallized from ethanol to obtain 1.9 g of 3-(4-chlorobenzyloxy)-N-cyclobutylmethyl-N-methylbenzylamine maleate.

White powder

Melting point: 102.5°–103.0° C.

The compounds of Examples 1–3 and 5–10 were obtained in the same manner as in Example 13 by using suitable starting materials.

Pharmacological Tests (1) Forced swimming test

This test was conducted by modifying the test methods described in Nature, Vol. 266, pp. 730–732 (1977) and European Journal of Pharmacology, Vol. 47, pp. 379–391 (1978). That is, a tap water (temp.: about 25° C.) was fed into a clindrical water bath (inside diameter: 29.5 cm, height: 25 cm) made of a transparent acrylic resin, to a water depth of 11.3 cm. Male mice of 7–8 week-age each weighing 30–35 g were forced to swim therein for 6 minutes, and the amount of swimming was measured. The measurement of amount of swimming was automatically made by the use of an infrared beam and a sensor capable of detecting the beam, and the number of counting was used as a yardstick indicating the depressive state of mouse. A larger number means a higher antidepressive activity of test compound used.

Each mouse was fasted for 16–18 hours before swimming and received oral administration of a test compound and a solvent 1 hour before the start of the test. The solvent was a physiological saline solution containing 5% of acasia, and the test compound was used by suspensing or dissolving in the solvent. Each mouse of control group received only the solvent, i.e. the physiological saline solution containing 5% of acasia.

The results are shown in Table 2. In Table 2, the values of swimming amount (%) are those when the value of control group was taken as 100%.

TABLE 2

| Test compound | Amount administered (mg/kg) | Amount of swimming (%) |
| --- | --- | --- |
| Example 1 compound | 1 | 120 |
| Example 2 compound | 3 | 110 |
| Example 3 compound | 30 | 118 |

(2) Elevated plus-maze test

This test was conducted in accordance with the test methods described in Pharmacology Biochemistry & Behavior, Vol. 24, pp. 525–529 (1986) and Psychopharmacology, Vol. 92, pp. 180–185 (1987). There was used, as the test apparatus, an acrylic resin-made maze consisting of a platform (5×5 cm), two open arms (each 5×5 cm and having no wall surrounding the arms) and two closed arms (each 25×5 cm and surrounded, at the three sides, by a transparent acrylic resin-made wall 15 cm high), wherein the two open arms extended from the two opposite sides of the platform and the two closed arms extended from the remaining two opposite sidss of the platform (the two open arms and the two closed arms formed a cross shape via the platform). The platform, open arms and closed arms of the maze were held at a height of 38 cm from the floor of a room in which the maze was placed. On the platform of the maze was placed a male mouse of 4–5 week-age weighing 20–24 g which had been fasted for 16–18 hours, with the face being directed to either of the open arms. For 5 minutes from that timing, the movement of the mouse on the maze was observed to measure the times of entry into open arms and the times of entry into closed arms. There was used, as the yardstick of anti-anxiety activity of test compound, there was used "frequency of entry into open arms" which is defined as follows.

Frequency (%) of entry into open arms=(times of entry into open arms)–(times of entry into open arms+times of entry into closed arms)×100

A larger frequency means a higher anti-anxiety activity of test compound.

Each test compound was suspended or dissolved in a physiological saline solution containing 5% of acasia and orally administered to each mouse 1 hour before the mouse was placed on te maze. Only the physiological saline solution was administered to each mouse of control group.

The results are shown in Table 3. In Table 3, the values of frequency (%) are those when the value of control group was taken as 100%.

TABLE 3

| Test compound | Amount administered (mg/kg) | Frequency (%) |
| --- | --- | --- |
| Example 1 compound | 1 | 262 |
| Example 2 compound | 3 | 175 |
| Example 3 compound | 3 | 128 |

(3) Evaluation of effect for ameliorating disorder of consciousness, in a coma forcibly caused by head trauma This test was conducted in accordance with the test methods described in Journal of Japan Accident Medical Association, Vol. 25, p. 202 (1977) and Journal of Clinical and Experimental Medicine (IGAKU NO AYUMI), Vol. 102, pp. 867–869 (1977). That is, male mice of 4–5 week-age each weighing 20–29 g were fasted for 18–20 hours; then, the head of each mouse was fixed to a foamed polystyrol-made pillow; an acrylic resin-made cylindrical bar was dropped, along a transparrent plastic tube, onto the vertex cranii of each mouse to give an impact to the mouse. The resulting disturbance of consciousness in mouse was examined by measuring the following two items: a time from the coma after impact to recovery of righting reflection (this time is referred to as RR time) and a time for said coma to recovery of spontaneous motility (this time is referred to as SM time). A test compound was suspended or dissolved in a physiological saline solution containing 5% of acasia and then orally administered to each mouse 1 hour before the mouse was subjected to anesthesia loading. Only the physiological saline solution containing 5% of acasia was administered to the mice of control group. The effect for ameliorating disturbance of consciousness, of each test compound was evaluated by a ratio (%) of RR or SM time of test compound-administered mice to RR or SM time of control group mice. Each of the present compounds tested showed a significant effect for ameliorating disturbance of consciousness.

(4) Test for amount of mouse's movement under controlled conditions (a) Test animals ddy-Strain male mice of 7–8 week-age each weighing 30–35 g.

(b) Test apparatus

A transparent acrylic resin-made test box of 30×30×29 cm having a grid floor; a photoelectric tester for measuring the amount of mouse's movement; and a shock generator for imparting an electrical shock to each mouse.

(c) Test procedure

On the first day, mice were placed in the above test apparatus and received an electrical shock (AC 160 V×3 A, 200 mse, 0.1 Hz) from the floor grid for 6 minutes. On the second day, the mice were returned to the same apparatus (but received no electrical shock) and measured for the amount of movement by using the above photoelectric tester (these mice were a condition-controlled group). The same procedure was applied to the mice of control group except that they received no electrical shock on the first day.

Each test compound was suspended in a physiological saline solution containing 5% of acasia, or dissolved in a physiological saline solution. The suspension or solution was orally administered to each mouse on the second day 30 minutes to 1 hour before the measurement of amount of movement. The parameter of the condition-controlled group was compared with that of the solvent alone-administered group (control group).

In this test, "parameter" is the amount of movement (the number of counting by the photoelectric tester) on the second day.

In the above test, the electrically-shocked mice, when returned to the same site, remember the shock and generate a stress; and this stress substantially reduce the amount of their movement. The present compounds tested were effective in recovering the amount of movement.

We claim:

1. A benzylamine derivative represented by the general formula (1):

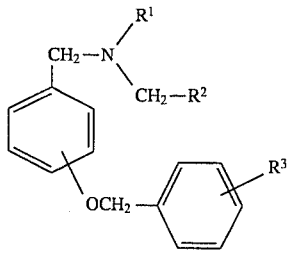

(1)

wherein $R^1$ is a lower alkyl group;

$R^2$ is a cycloalkyl group; and $R^3$ is a halogen atom;

or a salt thereof.

2. The benzylamine derivative or salt thereof according to claim 1, wherein $R^1$ is a methyl group or ethyl group.

3. The benzylamine derivative or salt thereof according to claim 2, wherein $R^1$ is a methyl group.

4. The benzylamine derivative or salt thereof according to claim 1, wherein $R^2$ is a cyclopropyl group or cyclobutyl group.

5. The benzylamino derivative or salt thereof according to claim 1, wherein $R^2$ is a cyclopropyl group.

6. The benzylamine derivative or salt thereof according to claim 1, wherein $R^3$ is a chlorine atom.

7. The benzylamine derivative or salt thereof according to claim 1, wherein $R^1$ is a methyl group or ethyl group; $R^2$ is a cyclopropyl group or cyclobutyl group; and $R^3$ is a chlorine atom.

8. The benzylamine derivative or salt thereof according to claim 6 or 7, wherein $R^3$ is substituted at 4-position in the benzene ring.

9. 3-(4-Chlorobenzyloxy)-N-cyclopropylmethyl-N-methylbenzylamine.

10. 4-(4-Chlorobenzyloxy)-N-cyclopropylmethyl-N-methylbenzylamine.

11. 2-(4-Chlorobenzyloxy)-N-cyclopropylmethyl-N-methylbenzyiamine.

12. A pharmaceutical composition comprising, as the active ingredient, a benzylamine derivative or salt thereof of claim 1 and a pharmaceutically acceptable carrier.

13. The pharmaceutical composition of claim 12, wherein the benzylamine derivative is selected from the group consisting of 3-(4-chlorobenzyloxy)-N-cyclopropylmethyl-N-methylbenzylamine, 4-(4-chlorobenzyloxy)-N-cyclopropylmethyl-N-methylbenzylamine, and 2-(4-chlorobenzyloxy)-N-cyclopropylmethyl-N-methylbenzylamine.

* * * * *